US006503263B2

United States Patent
Adams

(12) United States Patent
(10) Patent No.: US 6,503,263 B2
(45) Date of Patent: Jan. 7, 2003

(54) SURGICAL MICRO-SHAVING INSTRUMENT WITH ELEVATOR TIP

(75) Inventor: Kenneth M. Adams, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/839,319

(22) Filed: Apr. 20, 2001

(65) Prior Publication Data

US 2002/0038130 A1 Mar. 28, 2002

Related U.S. Application Data

(60) Provisional application No. 60/235,220, filed on Sep. 24, 2000.

(51) Int. Cl.$^7$ .............................................. A61B 17/32
(52) U.S. Cl. ........................................................ 606/170
(58) Field of Search ......................... 606/1, 159, 170, 606/171, 180, 167, 168, 185; 604/564–567

(56) References Cited

U.S. PATENT DOCUMENTS

| | | | |
|---|---|---|---|
| 3,844,272 A | * 10/1974 | Banko .......................... 606/170 |
| 4,368,734 A | 1/1983 | Banko | |
| 4,530,356 A | 7/1985 | Helfgott et al. | |
| 4,649,919 A | * 3/1987 | Thimsen et al. ............... 604/22 |
| 4,834,729 A | * 5/1989 | Sjostrom ..................... 606/170 |
| 4,850,354 A | 7/1989 | McGurk-Burleson et al. | |
| 4,986,825 A | * 1/1991 | Bays et al. ..................... 604/22 |
| 5,320,635 A | 6/1994 | Smith | |
| 5,685,838 A | 11/1997 | Peters et al. | |
| 5,695,511 A | 12/1997 | Cano et al. | |
| 5,735,792 A | 4/1998 | Vanden Hoek et al. | |
| 5,741,287 A | 4/1998 | Alden et al. | |
| 5,916,231 A | 6/1999 | Bays | |
| 5,922,003 A | 7/1999 | Anctil et al. | |
| 5,925,056 A | 7/1999 | Thomas et al. | |
| 5,957,881 A | 9/1999 | Peters et al. | |
| 5,957,945 A | 9/1999 | Bays | |
| 5,964,777 A | * 10/1999 | Drucker ....................... 606/180 |
| 6,001,116 A | 12/1999 | Heisler et al. | |
| 6,101,477 A | 1/2000 | Bays | |
| 6,068,641 A | * 5/2000 | Varsseveld .................. 606/170 |

FOREIGN PATENT DOCUMENTS

GB    2 205 045    11/1988

* cited by examiner

Primary Examiner—David O. Reip
(74) Attorney, Agent, or Firm—Curtis Kinghorn, Esq.; Timothy A. Czaja, Esq.

(57) ABSTRACT

A surgical micro-shaving instrument including an outer tubular member coaxially maintaining an inner tubular member. The outer tubular member is an elongated body defining a distal section, a proximal section and a central lumen extending from the distal section to the proximal section. The distal section forms an elevator tip and a cutting window. The cutting window is positioned proximal the elevator tip and is connected to the central lumen. The elevator tip terminates at a blade-like edge and is non-blunt. In one preferred embodiment, the elevator tip terminates in a knife edge. Regardless, the elevator tip defines a top surface extending from the elevator window. In one preferred embodiment, the top surface extends in an angular fashion, planar with a plane of the cutting window. In another preferred embodiment, the top surface includes a proximal portion and a distal portion. With this configuration, the proximal portion is planar with a plane of the cutting window. Further, the distal portion extends upwardly in an angular fashion from the proximal portion, defining an obtuse angle therebetween. During use, the surgical micro-shaving instrument is directed toward the inferior turbinate. The elevator tip is used to puncture the turbinate as well as to dissect tissue away from the turbinate bone, thereby creating improved tissue engagement.

20 Claims, 3 Drawing Sheets

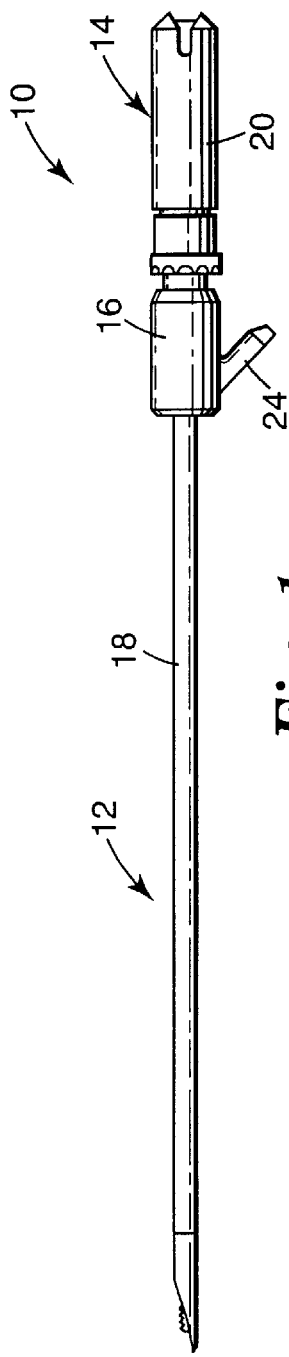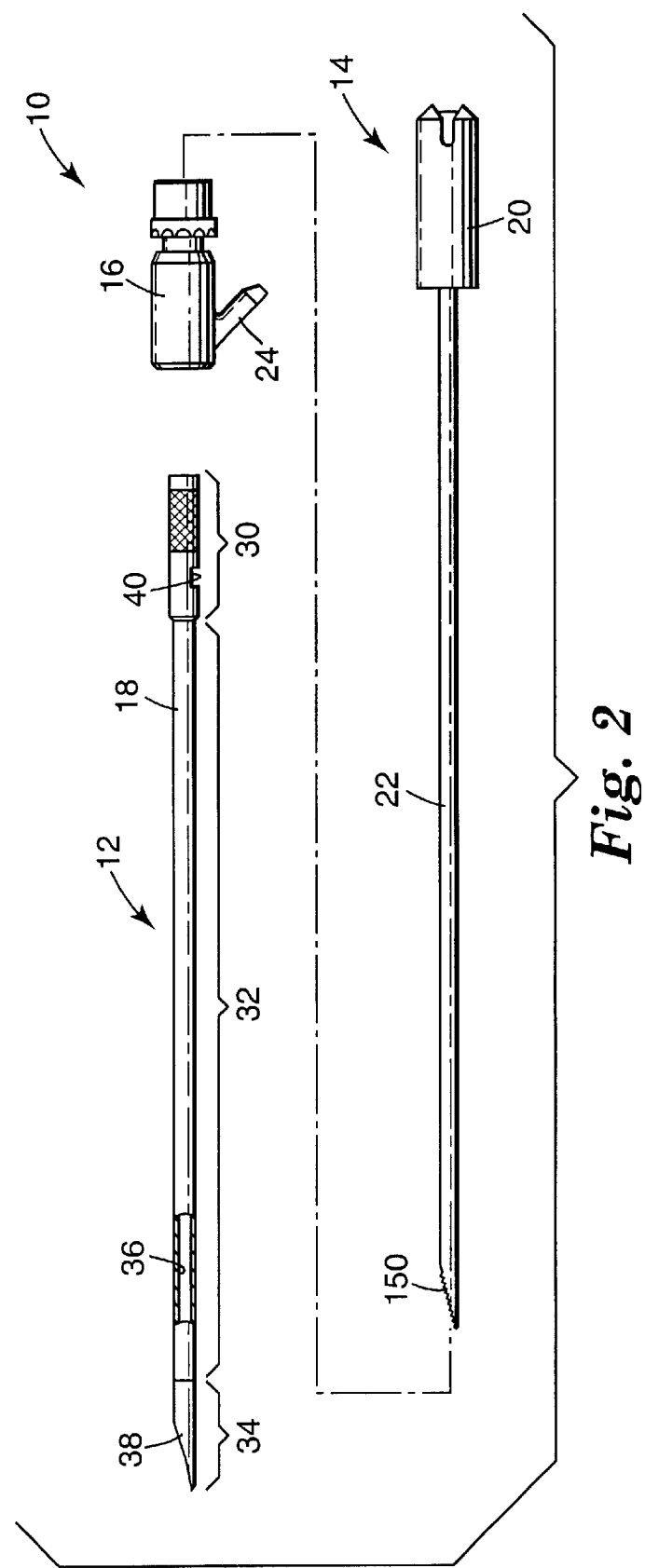

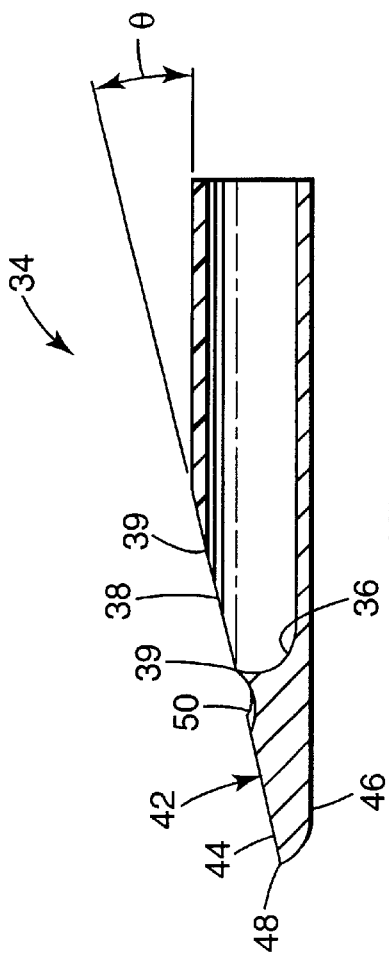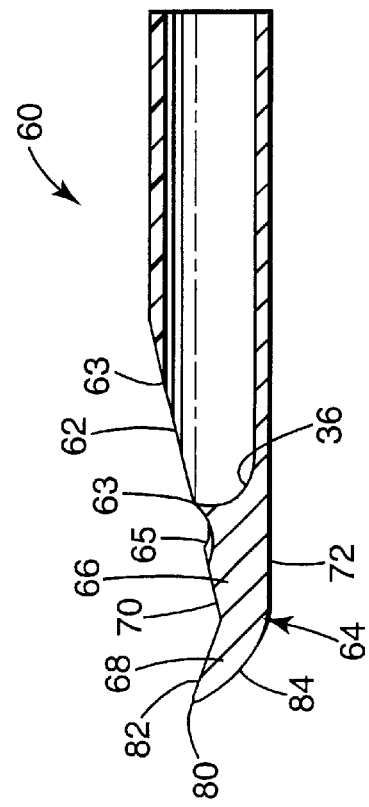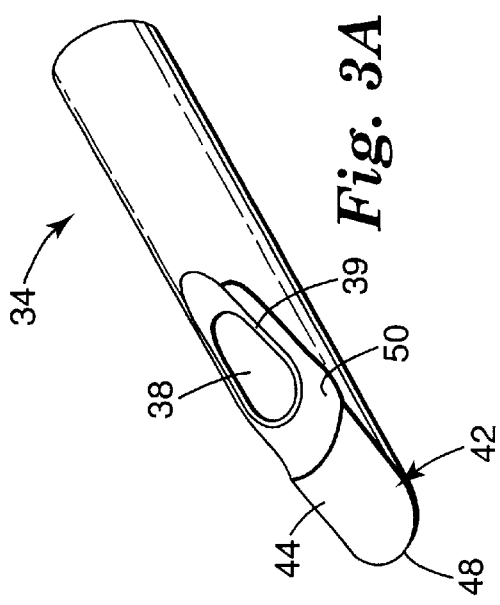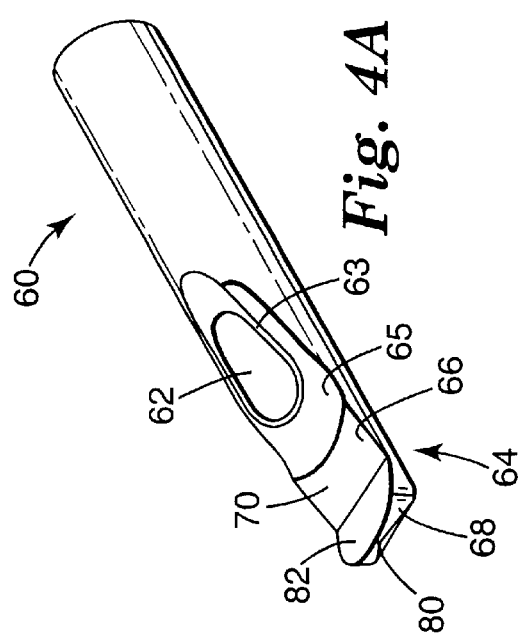

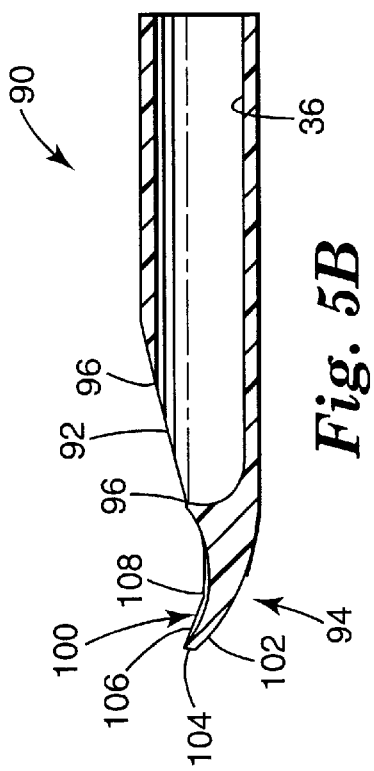
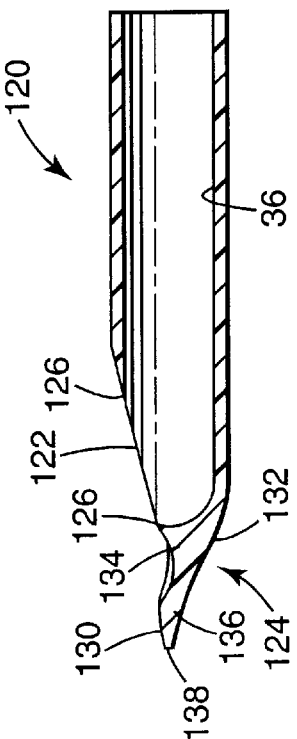
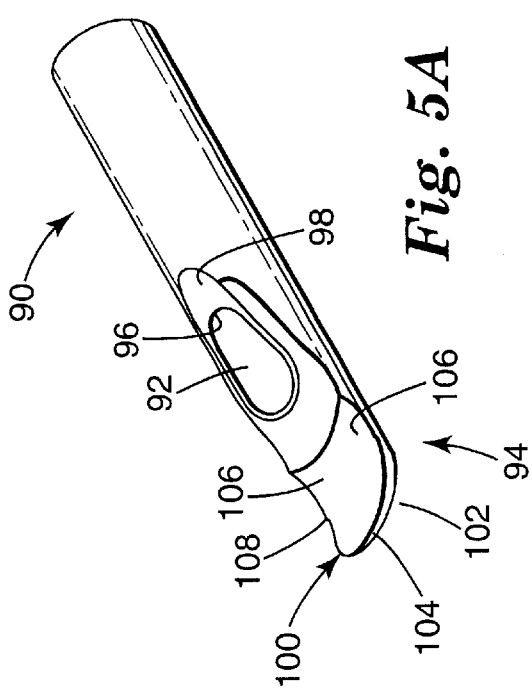
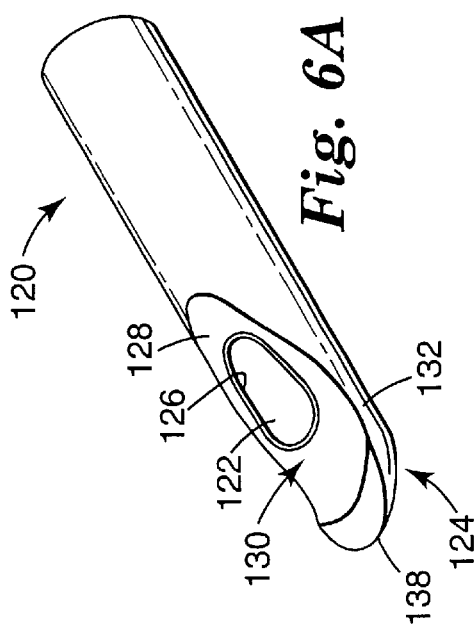

SURGICAL MICRO-SHAVING INSTRUMENT WITH ELEVATOR TIP

CROSS-REFERENCE TO RELATED APPLICATIONS

This application claims the benefit of U.S. Provisional Application No. 60/235,220, filed on Sep. 24, 2000.

BACKGROUND OF THE INVENTION

The present invention relates to a surgical cutting instrument. More particularly, it relates to a surgical micro-shaving instrument the distal tip of which is configured to assist in tissue dissection and is particularly useful for inferior turbinate reduction procedures.

Surgical resecting instruments in which an elongate inner member is rotated or oscillated within an elongate outer tubular member has become well accepted in surgical procedures where access to the surgical site is gained via a narrow portal or passage. Typically, the outer tubular member includes a distal end defining a cutting port or window, and the inner member includes a distal end with a cutting tip for engaging and resecting bodily tissue via the cutting window. Proximal ends of the inner and outer members are commonly secured to hubs that, in turn, attach to a handpiece. The handpiece can have a motor for rotating and/or oscillating the inner member relative to the outer tubular member. The cutting tip of the inner tubular member can have various configurations specific to the surgical procedure in question (e.g., resecting, cutting, shaving, abrading, etc.), with the cutting window being suitably configured to cooperate with the particular configuration of the cutting tip. Typically, the inner tubular member defines a lumen so that the loose tissue resulting from a cutting, resecting or abrading procedure can be aspirated from the target site.

The above-described surgical cutting instruments are useful for a number of surgical procedures, especially ear-nose-throat (ENT) operations. One particular ENT procedure relates to treatment of an inferior turbinate in the sinus cavity. The role of inferior turbinate pathology and the reduction of nasal airflow are well known. In short, the inferior turbinate of the sinus cavity may become enlarged or inflamed (e.g., inferior turbinate hypertrophy) for a variety of reasons. This inflammation obstructs the patient's nasal airway, causing breathing difficulties. In cases where medicinal treatment fails, a preferred surgical treatment entails resecting submucous tissue of the inferior turbinate, thereby reducing the inferior turbinate size. In this regard, available techniques for turbinate reduction include turbinectomy, submucous turbinectomy, inferior turbinoplasty, cryotherapy, submucous electrosurgery, and laser turbinoplasty. Unfortunately, short-term and long-term complications such as bleeding, crusting, synechiae formation, and atrophic rhinitis are often times associated with each of the above-listed techniques, due to sacrifice of mucosa for access to the target site. In light of these potential complications, surgeons have recently begun using the surgical cutting instruments previously described, and in particular a 2-mm surgical shaving instrument, to resect or shave tissue on an inside of the inferior turbinate by puncturing the turbinate anteriorly and then moving the cutting tip in a posterior fashion while resecting the targeted tissue. By resecting the interior tissue, the turbinate heals by shrinking internally, thereby allowing for better nasal airflow.

Use of a surgical micro-resecting or -shaving instrument for treatment of enlarged or inflamed inferior turbinate in the sinus cavity appears quite promising. In fact, a micro-shaving instrument is best able to achieve a primary goal of volumetric reduction of the sub-mucosal vascular stromal tissue with preservation of the overlying respitory epithelium. Unfortunately, currently available instruments for performing inferior turbinectomies have a blunt, distal end that is not conducive to a puncturing-type action. Further, available surgical micro-shaving instruments are configured such that the surgeon must rely solely upon the cutting window to resect the tissue from the bone inside the turbinate of the sinus cavity. This is a difficult and time consuming procedure, as the tissue in question is generally "tight" against the bone.

Inferior turbinate reduction with a surgical micro-shaving instrument appears highly viable, and may eliminate the complications otherwise associated with other turbinate reduction techniques. Unfortunately, however, currently available micro-shaving instruments are not designed to satisfy the needs of the inferior turbinate site. Therefore, a need exists for an inferior turbinate surgical micro-shaving instrument.

SUMMARY OF THE INVENTION

One aspect of the present invention relates to a surgical micro-shaving instrument including an outer tubular member coaxially maintaining an inner tubular member. The outer tubular member is an elongated body defining a distal section, a proximal section and a central lumen extending from the distal section to the proximal section. The distal section forms an elevator tip and a cutting window. The cutting window is positioned proximal the elevator tip and is connected to the central lumen. The elevator tip terminates at a blade-like edge and is non-blunt. In one preferred embodiment, the elevator tip terminates in a knife edge. Regardless, the elevator tip defines a top surface extending from the elevator window. In one preferred embodiment, the top surface extends in an angular fashion, planar with a plane of the cutting window. In another preferred embodiment, the top surface includes a proximal portion and a distal portion. With this configuration, the proximal portion is planar with a plane of the cutting window. Further, the distal portion extends upwardly in an angular fashion from the proximal portion, defining an obtuse angle therebetween.

During use, the surgical micro-shaving instrument is directed toward the inferior turbinate. The elevator tip is used to puncture the turbinate as well as to dissect tissue away from the turbinate bone, thereby creating improved tissue/instrument engagement.

BRIEF DESCRIPTION OF THE DRAWINGS

FIG. 1 is a side view of a surgical micro-shaving instrument in accordance with the present invention;

FIG. 2 is a side, exploded view of the instrument of FIG. 1;

FIG. 3A is an enlarged, perspective view of an elevator tip portion of the instrument of FIG. 1;

FIG. 3B is an enlarged, cross-sectional view of FIG. 3A;

FIG. 4A is an enlarged, perspective view of an alternative embodiment elevator tip in accordance with the present invention;

FIG. 4B is an enlarged, cross-sectional view of FIG. 4A;

FIG. 5A is an enlarged, perspective view of another alternative embodiment elevator tip in accordance with the present invention;

FIG. 5B is an enlarged, cross-sectional view of FIG. 5A;

FIG. 6A is an enlarged, perspective view of another alternative embodiment elevator tip in accordance with the present invention; and FIG. 6B is an enlarged, cross-sectional view of FIG. 6A.

DESCRIPTION OF THE PREFERRED EMBODIMENTS

One preferred embodiment of a surgical micro-shaving instrument or blade 10 is illustrated in FIG. 1. The micro-shaving instrument 10 includes an outer blade assembly 12 and an inner blade assembly 14. The outer blade assembly 12 includes an outer hub 16 and an outer tubular member 18, whereas the inner blade assembly 14 includes an inner hub 20 and an inner elongate member 22 (illustrated in FIG. 2). Similar to other available micro-shaving instruments, the inner elongate member 22 is sized to be coaxially received within the outer tubular member 18. However, as described in greater detail below, the micro-shaving instrument 10 is specifically configured to optimally perform an inferior turbinate reduction procedure.

As is known in the art, the outer tubular member 18 extends distally from the outer hub 16. To this end, the outer hub 16 can assume a wide variety of forms known in the art and may, for example, form an irrigation port 24. Alternatively, in an alternative embodiment, the micro-shaving instrument 10 can be configured to operate without the outer hub 16.

With additional reference to FIG. 2, the outer tubular member 18 is an elongated, tubular body defining a proximal section 30, an intermediate section 32, a distal section 34, and a central lumen 36. The outer tubular member 18 is formed from a relatively rigid, surgically safe material, preferably 304 stainless steel. The central lumen 36 extends from the distal section 34 to the proximal section 30. In this regard, and as described in greater detail below, the distal section 34 forms a cutting window 38 (shown generally in FIG. 2) in fluid communication with the central lumen 36. Similarly, the proximal section 30 forms an irrigation inlet 40 in fluid communication with the central lumen 36. Upon final assembly, the irrigation inlet 40 is aligned with the irrigation port 24 otherwise formed by the outer hub 16 such that fluids can be irrigated to the cutting window 38 via the central lumen 36.

The proximal section 30 has been depicted in FIG. 2 as having a slightly enlarged diameter to facilitate assembly to the outer hub 16. The remainder of the outer tubular member 18, however, is preferably sized for an inferior turbinate reduction procedure. In particular, the intermediate section 32, as well as a majority of the distal section 34 immediately proximal the cutting window 38, has, in one preferred embodiment, an outer diameter of 2 mm. Alternatively, the intermediate section 32, as well as a majority of the distal section 34 immediately proximal the cutting window 38, can have an outer diameter of 2.9 mm.

One preferred embodiment of the distal section 34 is shown in greater detail in FIGS. 3A and 3B. As previously described, the distal section 34 forms the cutting window 38, otherwise in fluid communication with the central lumen 36. The cutting window 38 is defined by a cutting window wall 39. In addition, the distal section 34 forms an elevator tip 42 extending distally from the cutting window 38. The elevator tip 42 includes opposing top and bottom surfaces 44, 46, as best shown in FIG. 3B. The surfaces 44, 46 taper in width distally, and terminate at an end 48 that is preferably relatively sharp or blade-like. Thus, the end 48 serves as a blade able to easily puncture tissue upon contact therewith.

As a point of reference, in one preferred embodiment, the blade end 48 has a thickness of 0.005 inch. Unlike currently available micro-shaving instruments, the elevator tip 42, and in particular the blade-like end 48, is non-blunt.

To facilitate enhanced tissue interaction at the cutting window 38, the distal section 34 preferably forms a recessed portion 50 about a majority of the cutting window 38. More particularly, and as best shown in FIG. 3B, the cutting window wall 39 is preferably formed and orientated such that the cutting window 38 extends distally in an angular fashion, whereby the distal section 34 tapers in height (relative to the horizontal orientation of FIG. 3B). This angular taper of the cutting window wall 39, and thus the cutting window 38, is represented by the angle θ in FIG. 3B, whereby θ is preferably in the range of approximately 10–16°, more preferably 13°. The recessed portion 50 is defined about the cutting window wall 39 such that the wall 39 effectively projects outwardly relative to the recessed portion 50. This outward projection provides a distinct surface with sharp edges for engaging and/or dissecting tissue.

The recessed portion 50 is preferably concave in shape distal the cutting window 38, as best illustrated in FIG. 3B. With this in mind, the top surface 44 preferably extends in a linear fashion from the recessed portion 50, tapering in height relative to the bottom surface 46. More particularly, a plane of the top surface 44 is preferably aligned with the plane defined by the cutting window wall 39. Thus, relative to horizontal, the top surface 44 defines an angle corresponding with the angle θ. Finally, the bottom surface 46 preferably curves to the end 48.

The above-described construction of the distal section 34, and in particular the elevator tip 42, is but one acceptable configuration. For example, an alternative distal section 60 is shown in FIGS. 4A and 4B.

Once again, the distal section 60 forms a cutting window 62 and an elevator tip 64 distal the cutting window 62. The cutting window 62 is defined by a cutting window wall 63. A recessed portion 65 is formed about a majority of the wall 63. The elevator tip 64 includes a proximal region 66 and a distal region 68, with the proximal region 66 extending from the recessed portion 65. The recessed portion 65 is formed about, and extends below, a majority of the cutting window wall 63, with the cutting window wall 63 tapering distally as with the embodiment of FIG. 3A. The recessed portion 65, in combination with the tapered extension of the cutting window 62, provides for enhanced exposure of a cutting tip (not shown) otherwise disposed within the central lumen 36 upon final assembly. Further, projection of the wall 63 above the recessed portion 65 provides a distinct surface with relatively sharp edges conducive for tissue engagement.

The proximal region 66 of the elevator tip 64 is relatively uniform in width, defined generally by a top surface 70 and a bottom surface 72. The top surface 70 extends from the recessed portion 65 that is otherwise concave distal the cutting window 62. As shown in FIG. 4B, the top surface 70 extends in an angular fashion from the recessed portion 65, tapering in height relative to the bottom surface 72. The angular orientation of the top surface corresponds with the angular taper defined by the cutting window wall 63. Thus, the top surface 70 is generally aligned, or planar, with a plane defined by the cutting window wall 63.

The distal region 68 extends from the proximal region 66 and terminates in a blade end 80. As best shown in FIG. 4A, the distal region 68 tapers in width, such that the blade end 80 is a relatively sharp tip capable of piercing or puncturing bodily tissue with minimal applied force. As with the proximal region 66, the distal region 68 includes a top surface 82 and a bottom surface 84. As best shown in FIG. 4B, the top surface 82 of the distal region 68 extends in an angular fashion, upwardly from the top surface 70 of the proximal region 66. In a preferred embodiment, the top surface 82 of the distal region 68 and the top surface 70 of the proximal region 66 form an obtuse angle in the range of approximately 130°–160°, more preferably 147°. The bottom surface 84 of the distal region 68 extends from the bottom surface 72 of the proximal region 66 in a curved or arcuate fashion to the blade end 80. With this configuration, the elevator tip 64, and in particular the distal region 68, is optimally shaped to promote deployment of the surgical micro-shaving instrument 10 (FIG. 1) at the inferior turbinate (not shown), as well as to resect tissue. Further, the curved bottom surface 84 of the distal region 68 facilitates reciprocating movement of the distal section 60 within the inferior turbinate during a resecting or shaving procedure.

Yet another alternative embodiment distal section 90 is shown in FIGS. 5A and 5B. The distal section 90 forms a cutting window 92 and an elevator tip 94 distal the cutting window 92. The cutting window 92 is defined by a cutting window wall 96. A recessed portion 98 is formed about a majority of the wall 96, as best illustrated in FIG. 5A. Unlike the distal sections 34, 60, previously described, the recessed portion 98 extends only slightly distal the cutting window wall 96. In other words, the distal section 90 transitions from the cutting window 92 to the elevator tip 94 immediately distal the cutting window 92. In this regard, the elevator tip 94 is defined by a top surface 100 and a bottom surface 102. The top surface 100 is preferably concave, extending downwardly from the cutting window wall 96. In effect, the downward extension of the top surface 100 corresponds with the recessed portions 50 (FIG. 3A), 65 (FIG. 4A) previously described. The concave nature of the top surface 100, in combination with the distal taper of the cutting window 92, provides for enhanced exposure of a cutting tip (not shown) otherwise disposed within the central lumen 36 upon final assembly.

The elevator tip 94 provides additional preferred features. First, the elevator tip 94 terminates in a blade end 104. As best shown in FIG. 5A, the elevator tip 94 tapers distally in width, such that the blade end 104 is a relatively sharp tip capable of piercing or puncturing bodily tissue with minimal applied force. Further, the bottom surface 102 is preferably curved so as to facilitate reciprocating movement of the distal section 90 within the inferior turbinate (not shown) during a resecting or shaving procedure. Also, the top surface 100 is defined by opposing edges 106. As best shown in FIG. 5B, one or more serrations 108 are formed in the edges 106. These serrations 108 are configured to readily resect or shave contacted tissue.

Yet another alterative embodiment distal section 120 is shown in FIGS. 6A and 6B. The distal section 120 forms a cutting window 122 and an elevator tip 124 distal the cutting window 122. The cutting window 122 is defined by a cutting window wall 126. A recessed portion 128 is formed about a majority of the wall 126, as best illustrated in FIGS. 6A. Similar to the distal section 90 (FIG. 5A and 5B), the recessed portion 128 extends only slightly distal the cutting window wall 126. In other words, the distal section 120 transitions from the cutting window 122 to the elevator tip 124 immediately distal the cutting window 122. Also, as with previous embodiments, the cutting window wall 126 tapers distally relative to a central axis of the distal section 120.

The elevator tip 124 includes a top surface 130 and a bottom surface 132 extending along a first section 134 and a second section 136. The elevator tip 124 terminates in a blade end 138. As best shown in FIG. 6A, the elevator tip 124 tapers distally in width, such that the blade end 138 is a relatively sharp tip capable of piercing or puncturing bodily tissue with minimal applied force.

With respect to the first section 134 of the elevator tip 124, the top surface 130 is preferably concave, forming a depression relative to a distal end of the cutting window wall 126. For example, in one preferred embodiment, the top surface 130 at the first section 134 defines, in longitudinal cross-section, a concave curve having a radius of approximately 0.06 inch, although other dimensions are acceptable. Regardless, this preferred attribute provides for enhanced exposure of a cutting tip (not shown) otherwise disposed within the central lumen 36 upon final assembly.

The bottom surface 132 is curved along the first and second sections 134, 136. However, unlike previous embodiments, the bottom surface 132 forms a concave curve in longitudinal cross-section (as shown in FIG. 6B) as the bottom surface 132 transitions from the first section 134 to the second section 136. This one preferred configuration promotes advancement of the elevator tip 124 posteriorly through the inferior turbinate (not shown). In one preferred embodiment, a curve of the bottom surface 132 is such that, relative to the cross-sectional view of FIG. 6B, the bottom surface 132 elevates from the first section to the blade end 138 a preferred distance (or height) in the range of 0.056–0.06 inch, most preferably 0.058 inch. Alternatively, other dimensions can be employed.

Regardless of exact form, in one preferred embodiment, the distal section 34 (FIG. 3A), 60 (FIG. 4A), 90 (FIG. 5A), or 120 (FIG. 6A) is formed separate from a remainder of the outer tubular member 18 (FIG. 2), and subsequently assembled thereto. With this fabrication technique, the distal section 34, 60, 90, 120 can be formed from a material more amenable to precise manufacturing tolerances. For example, in one preferred embodiment, the distal section 34, 60, 90, 120 is formed from heat treated, 17-4 stainless steel, whereas a remainder of outer tubular member 18 is a 304 stainless steel material. Regardless, the so-formed distal section 34, 60, 90, 120 is secured to the intermediate section 32 of the outer tubular member 18, such as by a laser weld.

Returning to FIG. 2, the inner blade assembly 14 is of a type commonly known in the art, whereby the inner tubular member 22 extends from the inner hub 20. In one preferred embodiment, the inner hub 20 is configured for selective attachment to a handpiece (not shown) that can be operated to automatically maneuver the inner blade assembly 14 during use.

The inner tubular member 22 forms a cutting tip 150 at a distal end thereof. Upon final assembly, and with respect to the one embodiment of in FIG. 1, the inner tubular member 22 is coaxially disposed within the outer tubular member 18 such that the cutting tip 150 is exposed through the cutting window 38. The cutting tip 150 can assume a wide variety of forms, and preferably forms a series of teeth or cutting edges designed to engage and resect (or shave) tissue.

As previously described, the surgical micro-shaving instrument 10 of the present invention is particularly useful for an inferior turbinate reduction procedure. In one preferred embodiment, the assembled instrument 10 is deployed to the sinus cavity, with the blade end 48 (FIG. 3A), 80 (FIG. 4A), 104 (FIG. 5A), or 138 (FIG. 6A) being inserted into the anterior face of the inferior turbinate just medial to the muco-cutaneous junction. The blade end 48, 80, 104, or 138 is then firmly pushed towards the turbinate bone, piercing through the turbinate mucosa. In this regard, because the blade end 48, 80, 104, 138 is relatively sharp, the tissue is readily punctured, in direct contrast to blunt-ended instruments currently available. The distal section 34 (FIG. 3A), 60 (FIG. 4A), 90 (FIG. 5A), 120 (FIG. 6A) is then moved in a posterior fashion to resect submucous of the inferior turbinate. In one preferred embodiment, a submucosal pocket is dissected by tunneling the distal section 34, 60, 90, 120 in an anterior to posterior and superior to inferior sweeping motion. Once an adequate pocket has been established, tissue resection is initiated, preferably with the cutting tip 150 facing laterally and moving back and forth in a sweeping motion analogous to liposuction. Regardless, both the cutting tip 150 of the inner tubular member 22, as well as the cutting window wall 39 (FIG. 3A), 63 (FIG. 4A), 96 (FIG. 5A), or 122 (FIG. 6A) that otherwise projects relative to a remainder of the elevator tip 42 (FIG. 3A), 64 (FIG. 4A), or 94 (FIG. 5A), or 124 (FIG. 6A), respectively, assist in engaging and resecting contacted tissue. Further, with the embodiment of FIGS. 5A and 5B the serrations 108 formed by the edges 106 further assist in engaging and resecting contacted tissue. In effect, the elevator tip 42, 64, 94, 124 dissects tissue away from the bone inside of the turbinate, so that the cutting tip 150 of the inner tubular member 22 can more easily contact, and therefore resect or shave, desired tissue. The handpiece (not shown) is operated to cause the cutting tip 150 to rapidly resect or shave the contacted tissue, with the removed tissue being suctioned away from the target site.

The surgical micro-shaving instrument of the present invention provides a marked improvement over previous designs. With respect to inferior turbinate reduction procedures, use of a micro-shaving tool provides a distinct advantage over other available techniques (such as cryosurgery, electrocautery, laser, etc.) as the tool does not destroy mucousa in order to access the submucous tissue to be resected. In addition, as compared to available 2 mm and 2.9 mm micro-shaving tools, the elevator tip associated with the present invention readily pierces the inferior turbinate, as well as dissecting targeted tissue away from the turbinate bone, thereby promoting more efficient and effective cutting.

Although the present invention has been described with reference to preferred embodiments, workers skilled in the art will recognize that changes can be made in form and detail without departing from the spirit and scope of the present invention.

What is claimed:

1. A surgical micro-shaving instrument comprising:
   an inner tubular member forming a distal cutting tip; and
   an outer tubular member including a proximal section, a distal section, and a central lumen extending from the proximal section to the distal section sized to moveably receive the inner tubular member, the distal section forming:
      a cutting window fluidly connected to the central lumen, the cutting window being circumscribed by a cutting window wall and configured to selectively expose a portion of the cutting tip upon final assembly,
      an elevator tip extending distal the cutting window, the elevator tip terminating in a blade end configured to pierce contacted tissue.

2. The instrument of claim 1, wherein the cutting window wall defines an angular taper in the range of 10–16°.

3. The instrument of claim 1, wherein the distal section further forms a recessed portion about at least a portion of the cutting window wall.

4. The instrument of claim 1, wherein the elevator tip includes a bottom surface, at least a distal section of which is curved.

5. The instrument of claim 1, wherein the elevator tip includes a top surface, at least a proximal portion of which extends below the cutting window wall relative to a central axis of the outer tubular member.

6. The instrument of claim 5, wherein at least the proximal portion of the top surface extends distally in an angular fashion relative to the central axis of the outer tubular member.

7. The instrument of claim 6, wherein at least the proximal portion of the top surface and the cutting window wall are longitudinally co-planar.

8. The instrument of claim 7, wherein the top surface further includes a distal portion contiguous with the proximal portion.

9. The instrument of claim 7, wherein the top surface further includes a distal portion extending upwardly from the proximal portion relative to the central axis of the outer tubular member.

10. The instrument of claim 9, wherein an obtuse angle is formed by the proximal and distal portions of the top surface.

11. The instrument of claim 5, wherein the top surface is concave in longitudinal cross-section.

12. The instrument of claim 11, wherein the top surface is defined by opposing edges, at least one of which forms a serration.

13. The instrument of claim 1, wherein the blade end has a longitudinal cross-sectional thickness of 0.005 inch.

14. The instrument of claim 1, wherein the distal section has a diameter of 2 mm proximal the cutting window.

15. The instrument of claim 1, wherein the distal section has a diameter of 2.9 mm proximal the cutting window.

16. A method of reducing an inferior turbinate of a sinus cavity, the method comprising:
    providing a surgical instrument including an inner tubular member coaxially disposed within an outer tubular member, the outer tubular member including a distal section forming a cutting window and an elevator tip extending distal the cutting window, wherein the cutting window is configured to expose a cutting tip formed by the inner tubular member, and further wherein the elevator tip terminates in a blade end;
    deploying the surgical instrument to the sinus cavity;
    piercing the inferior turbinate with the blade and the elevator tip;
    moving the distal end in a posterior fashion; and
    resecting submucous tissue of the inferior turbinate.

17. The method of claim 16, wherein resecting submucous tissue includes: engaging the submucous tissue with the elevator tip.

18. The method of claim 17, wherein resecting the submucous tissue further includes:
    dissecting the submucous tissue away from a turbinate bone with the elevator tip; and
    resecting the dissected tissue with the cutting tip.

19. The method of claim 16, wherein the cutting window is circumscribed by a cutting window wall, a recessed portion being formed in the distal section about at least a portion of the cutting window wall, and further wherein resecting the submucous tissue includes:
    engaging the submucous tissue with the cutting window wall in a region of the recessed portion.

20. The method of claim 16, wherein the elevator tip includes a curved, bottom surface, and further wherein resecting submucous tissue includes:
    maneuvering the distal section in a reciprocating fashion within the inferior turbinate by sliding the curved, bottom surface along the inferior turbinate tissue.

* * * * *

UNITED STATES PATENT AND TRADEMARK OFFICE
Certificate

Patent No. 6,503,263 B2                                    Patented: January 7, 2003

On petition requesting issuance of a certificate for correction of inventorship pursuant to 35 U.S.C. 256, it has been found that the above identified patent, through error and without any deceptive intent, improperly sets forth the inventorship.
 Accordingly, it is hereby certified that the correct inventorship of this patent is: Laurence Roe O'Halloran, Arlington, VA; Timothy Bognar, Riverview FL; Miroslav Mitusina, Ruskin, FL; and Kenneth M. Adams, Jacksonville, FL.

Signed and Sealed this Twenty-Second Day of July 2003.

MICHAEL MILANO
*Supervisory Patent Examiner*
Art Unit 3731